(12) United States Patent
Lindner et al.

(10) Patent No.: US 6,323,350 B1
(45) Date of Patent: Nov. 27, 2001

(54) PROCESS FOR THE OXIDATION OF OLEFINS TO OLEFIN OXIDES

(75) Inventors: Joerg Lindner, Himmelpforten; Wolfgang Taeuber, Oldendorf; Hans-Juergen Wertgen, Himmelpforten, all of (DE)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/582,154

(22) PCT Filed: Dec. 17, 1998

(86) PCT No.: PCT/US98/26816

§ 371 Date: Jun. 21, 2000

§ 102(e) Date: Jun. 21, 2000

(87) PCT Pub. No.: WO99/32469

PCT Pub. Date: Jul. 1, 1999

(30) Foreign Application Priority Data

Dec. 22, 1997 (GB) .................................................. 9727117

(51) Int. Cl.⁷ ................................................ C07D 301/06
(52) U.S. Cl. ............................................................ 549/532
(58) Field of Search ............................................... 549/532

(56) References Cited

U.S. PATENT DOCUMENTS

| | | | |
|---|---|---|---|
| 3,071,601 | 1/1963 | Aries ................... | 260/348.5 |
| 3,238,229 | 3/1966 | Reid ................... | 260/348.5 |
| 3,350,418 | 10/1967 | Bowe et al. ........... | 260/348.5 |
| 3,428,658 | 2/1969 | Kassal ................ | 260/348.5 |
| 3,505,359 | 4/1970 | Rai et al. ............ | 260/348.5 |
| 3,518,285 | 6/1970 | Fenton et al. ......... | 260/348.5 |
| 3,716,562 | 2/1973 | Pregaglia et al. ...... | 260/348.5 |
| 3,957,690 | 5/1976 | Bobolev et al. ....... | 252/462 |
| 4,420,625 | 12/1983 | Sanderson et al. ..... | 549/533 |

FOREIGN PATENT DOCUMENTS

| | | | |
|---|---|---|---|
| DD 212 902 | 8/1984 | (DE) ............... | B01J/23/16 |
| DD 212 959 | 8/1984 | (DE) ............... | C07D/301/06 |
| DD 212 960 | 8/1984 | (DE) ............... | C07D/301/06 |
| DD 212 961 | 8/1984 | (DE) ............... | C07D/301/06 |
| DD 213 436 | 9/1984 | (DE) ............... | C07D/301/06 |
| DD 218 099 | 1/1985 | (DE) ............... | C07D/301/06 |
| DD 218 100 | 1/1985 | (DE) ............... | C07D/301/06 |
| WO 96/20788 | 7/1996 | (WO) .............. | B01J/31/16 |

OTHER PUBLICATIONS

Derwent—XP–002099550—SU 483391 Aug. 26, 1976—Propylene oxide and acetaldehyde prodn.–by oxygen oxidn. of proplene in series of chambers reducing prop;ylene oxygen ratio after first stage.—Shevchuk V.U.

Primary Examiner—T. A. Solola

(57) ABSTRACT

The present invention relates to a liquid phase process for preparing an olefin oxide from an olefin in a cascade of two or more reactors, in a baffled tank reactor or in a plug flow reactor which process comprises the steps of a) contacting the olefin in a solvent with oxygen or an oxygen-containing gas in a first reactor of the reactor cascade or in a first stage of the baffled tank reactor or of the plug flow reactor, thereby producing a mixture comprising olefin oxide, non-converted olefin, solvent and by-products and b) transferring at least a portion of the mixture obtained in step a) to a second reactor of the reactor cascade or to a second stage of the baffled tank reactor or plug flow reactor, adding an additional amount of i) oxygen or an oxygen-containing gas and/or ii) olefin to the mixture and continuing the reaction.

20 Claims, No Drawings

PROCESS FOR THE OXIDATION OF OLEFINS TO OLEFIN OXIDES

This application is A 371 of PCT/US98/26816 filed Dec. 17, 1998.

This invention pertains to a liquid phase process for the direct oxidation of olefins, such as propylene, by oxygen to olefin oxides, such as propylene oxide.

Olefin oxides, such as propylene oxide, are used to alkoxylate alcohols to form polyether polyols, such as polypropylene polyether polyols, which find significant utility in the manufacture of polyurethanes and synthetic elastomers. Olefin oxides are also important intermediates in the manufacture of alkylene glycols, such as propylene glycol and dipropylene glycol, and alkanolamines, such as isopropanolamine, which are useful as solvents and surfactants.

Propylene oxide is produced commercially via the well-known chlorohydrin process wherein propylene is reacted with an aqueous solution of chlorine to produce a mixture of propylene chlorohydrins. The chlorohydrins are dehydrochlorinated with an excess of alkali to produce propylene oxide.

Gas phase processes for the direct oxidation of olefins by molecular oxygen to the corresponding olefin have also been described in several publications.

Also liquid phase processes for the direct oxidation of olefins have been described in several publications.

DD-A-212 961 discloses a process for the oxidation of olefins containing 3 to 20 carbon atoms with oxygen-containing gases in liquid phase in the presence of transition metal complexes. The catalyst preferably is a mixture of a Cu(ll) complex compound and a complex compound of molybdenum or wolfram. The oxidation is carried out at a temperature of from 20° C. to 200° C. at atmospheric pressure or at an elevated pressure of 2 to 10 MPa. Recommended solvents are benzene, chlorobenzene, o-dichlorobenzene, nitrobenzene or bromobenzene. The desired products are obtained by fractional distillation of the product mixture.

U.S. Pat. No. 3,238,229 relates to a process for preparing olefin oxides wherein an olefinically unsaturated hydrocarbon is oxidized with molecular oxygen at a temperature of from 50° C. to 400° C. and a pressure of from 0.5 to 150 atmospheres in halogenated benzenes, such as o-dichlorobenzene, as a solvent. An oxygen-containing gas may be introduced into the olefin-solvent mixture in a continuously stirred reactor incrementally or continuously. The desired products are recovered from the reactor effluent by conventional separation techniques, such as distillation.

U.S. Pat. No. 3,350,418 discloses a liquid phase oxidation of propene with molecular oxygen in an ester, such as a fully esterified polyacyl ester, as a solvent. The oxidation is followed by a complex separation scheme.

U.S. Pat. No. 3,071,601 relates to the production of propylene oxide wherein propylene is oxidized with elemental oxygen in the liquid phase in a hydrocarbon solvent at elevated pressure and temperature in the presence of a catalyst.

U.S. Pat. No. 3,428,658 relates to the production of propylene oxide wherein propylene is reacted with oxygen in the presence of a solvent mixture comprising a saturated cyclic hydrocarbon and a chlorinated benzene. The reaction is carried out in a stainless-steel shaker tube. The U.S. patent mentions that better results are achieved when additional oxygen or oxygen-containing gas is added in small increments after the reaction temperature has been reached, since the reaction under oxygen-starved conditions tends to prevent degradation of the olefin oxide to by-products thereof.

U.S. Pat. No. 3,716,562 relates to the preparation of olefin oxides by the cooxidation of olefins and aldehydes with oxides in a liquid phase. A glass microreactor is used wherein the oxygen is continuously fed.

The higher the percentage of solvent that is in the liquid phase processes for the direct oxidation of olefins, the higher are the costs for the separation of the solvent from the product mixture, purification and recycling of the solvent. Considering that the production of olefin oxides, such as propylene oxide, from the corresponding olefin is carried out on a very large scale, it would be desirable to provide a liquid phase process for preparing an olefin oxide from an olefin which requires a decreased amount of solvent.

The present invention relates to a liquid phase process for preparing an olefin oxide from an olefin in a cascade of two or more reactors, in a baffled tank reactor or in a plug flow reactor which process comprises the steps of a) contacting the olefin in a solvent with oxygen or an oxygen-containing gas in a first reactor of the reactor cascade or in a first stage of the baffled tank reactor or of the plug flow reactor, thereby producing a mixture comprising olefin oxide, non-converted olefin, solvent and by-products and b) transferring at least a portion of the mixture obtained in step a) to a second reactor of the reactor cascade or to a second stage of the baffled tank reactor or plug flow reactor, adding an additional amount of i) oxygen or an oxygen-containing gas and/or ii) olefin to the mixture and continuing the reaction.

It has been surprisingly found that in the process of this invention wherein A) a cascade of two or more reactors is used and oxygen or an oxygen-containing gas and/or olefin is fed to several reactors or B) a baffled tank reactor or a plug flow reactor is used and oxygen or an oxygen-containing gas and/or olefin is fed in several portions, to several feed points of the reactor, the required amount of solvent per unit of produced olefin oxide can be substantially reduced. In large scale processes for olefin oxide production, this leads to a considerable reduction in production costs.

Ethylene can be employed in the process of this invention, however the olefin preferably contains three or more carbon atoms. Undiluted olefins or mixtures thereof are preferably used, however also olefin feedstock can be used which contains up to 50 weight percent of saturated compounds. Monoolefins are preferred, but compounds containing two or more olefins, such as dienes, can also be used. The olefins can be aliphatic or alicyclic. The olefin can be a simple hydrocarbon containing only carbon and hydrogen atoms; or alternatively, the olefin can be substituted at any of the carbon atoms with an inert substituent. The term "inert", as used herein, requires the substituent to be non-reactive in the process of this invention. Suitable inert substituents include, but are not limited to, halides, ether, ester, alcohol, or aromatic moieties, preferably chloro, $C_{1-12}$-ether, ester, or alcohol moieties or $C_{6-12}$-aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, -methylstyrene, divinylbenzene, allyl chloride, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$-olefin, more preferably, an unsubstituted or substituted-$C_{3-10}$-olefin. Most preferably, the olefin is propylene. Propylene feedstock can be used which contains up to 50 weight percent propane, however, the use of undiluted propylene is preferred. Accordingly, the subsequent detailed description of the present invention often relates to a process wherein propylene is used as a starting material, although the process of the present invention is not limited thereto.

The quantity of olefin employed in the process can vary over a wide range provided that the corresponding olefin oxide is produced. Generally, the quantity of olefin depends upon the specific process features, including, for example, the design of the reactor, the specific olefin, and economic and safety considerations. Those skilled in the art will know how to determine a suitable range of olefin concentrations for the specific process features. Typically, on a molar basis an excess of olefin is used relative to the oxygen. This condition enhances the selectivity to olefin oxide and minimizes the selectivity to combustion products, such as carbon dioxide. The quantity of the olefin is typically greater than 1, preferably greater than 10, more preferably greater than 20, and most preferably greater than 25 mole percent, based on the total moles of olefin, oxygen and solvent. Typically, the quantity of the olefin is less than 99, preferably less than 95, more preferably less than 90, and most preferably less than 80 mole percent, based on the total moles of olefin, oxygen and solvent.

The olefin is contacted with oxygen, such as essentially pure molecular oxygen, or an oxygen-containing gas, such as air or oxygen diluted with nitrogen or carbon dioxide. If the olefin is contacted with an oxygen-containing gas, the oxygen concentration in the gas preferably is from 15 to 60 volume percent, more preferably from 20 to 55 volume percent. Other sources of oxygen may be suitable, including ozone and nitrogen oxides, such as nitrous oxide. Air, molecular oxygen or oxygen diluted with carbon dioxide are preferred. The quantity of oxygen employed can vary over a wide range provided that the quantity is sufficient for producing the desired olefin oxide. Ordinarily, the number of moles of oxygen per mole of olefin is less than 1. Generally, the quantity of oxygen is greater than 0.01, preferably greater than 1, and more preferably greater than 2 mole percent, based on the total moles of olefin, oxygen, and solvent. Generally, the quantity of oxygen is less than 35, preferably less than 30, more preferably less than 25, and most preferably less than 20 mole percent, based on the total moles of olefin, oxygen and solvent.

The process of the present invention is carried out in liquid phase in a solvent. Solvents which can be used in a liquid phase process for preparing an olefin oxide are generally known in the art, for example, hydrocarbons, preferably aromatic hydrocarbons, ketones or esters, such as fully esterified polyacyl esters. However, in the process of the present invention preferably a solvent is used which has a boiling point above 130° C., preferably above 150° C., more preferably above 170° C. Preferred solvents are halogenated benzenes, particularly monohalogenated benzenes and, more preferably, dihalogenated benzenes. Exemplary thereof are monobromobenzene, chlorobenzene, o-, m- or p-dibromobenzene, o-, m- or p-bromochlorobenzene, or, most preferably, o-, m- or p-dichlorobenzene. The most preferred solvent for the process of the present invention is o-dichlorobenzene or m-dichlorobenzene. Other suitable solvents are polyethers, polyesters, polyalcohols or halogenated, preferably chlorinated, aliphatic alcohols, such as 2-chloro-1-propanol, 3-chloro-1-propanol, 1-bromo-2-propanol, dichloro- or dibromo-propanols, provided that these solvents are liquid at the chosen reaction conditions and have a boiling point above 130° C. The amount of solvent is typically greater than 0.1, preferably greater than 10, and more preferably greater than 15 mole percent, based on the total moles of olefin, oxygen and solvent. The amount of solvent is typically less than 90, preferably less than 80, and more preferably less than 75 mole percent, based on the total moles of olefin, oxygen and solvent.

The process of the present invention can be carried out in the absence or in the presence of a catalyst. if a catalyst is used, homogeneous or heterogeneous catalysts are useful. Exemplary of heterogeneous catalysts are those disclosed in East German Patent Nos. DD-218,100; DD-213,436; DD-218,099; DD-212,959; DD 212,960; DD-212 902; U.S. Pat. No. 3,957,690 and in published PCT application WO 96/20788. The disclosed heterogeneous catalysts contain active components, such as nickel, manganese, molybdenum and/or vanadium containing complexes or salts, on a carrier, such as an alumina, silica, aluminosilicate, titania, magnesia and/or carbon. As homogeneous oxidation catalysts common complexes or salts can be used, for examples those disclosed in U.S. Pat. Nos. 3,505,359; 3,518,285; or 4,420,625 or in WO 96/37295.

Typical active components of these catalysts are elements of groups Ib, IIb, IIIb, IVb, Vb, VIb, VIIb, IIIa, IVa, Va, VIa, VIII, and/or of the lanthanide group, such as Mo, Mn, Wo, Zn, Re, Au, Pd, Ag, V, Ru, La and/or Ti in any combination and ratio, but also Sc, Y, Ce, Zr, Nb, Ta, Cr, Fe, Os, Co, Rh, Ir, Ni, Pd, Pt, Cu, Ga, In, Ge, Sn, Se, Te, As, Sb and/or Bi in any combination and ratio with those mentioned above.

Furthermore, the process of the present invention can be carried out in the absence or in the presence of a promoter. A promoter is for example an aldehyde, like acetaldehyde, or an alkaline additive, like hydroxides of the group 1a and 1b, such as sodium hydroxide or magnesium hydroxide. The total quantity of promoter metal(s) generally is greater than 0.01, preferably greater than 0.10, and more preferably, greater than 0.15 weight percent, based on the total weight of the catalyst. The total quantity of promoter metal(s) is generally less than 20, preferably less than 15, and more preferably less than 10 weight percent, based on the total weight of the catalyst.

Preferably, the process of the present invention, that is, step a) and step b), is conducted at a temperature of from 100° C. to 210° C., more preferably from 130° C. to 190° C., most preferably from 150° C. to 180° C. Preferably, the pressure ranges from 20 to 100 bar (2 to 10 MPa), more preferably from 40 to 80 bar (4 to 8 MPa), most preferably from 50 to 60 bar (5 to 6 MPa) absolute. The reaction is generally completed within 2 to 450 minutes, typically within 5 to 300 minutes, in most cases within 8 to 200 minutes, depending on the reaction temperature and pressure.

The process of this invention can be conducted in a cascade of two or more reactors of any conventional design suitable for liquid phase processes. These designs include fixed-bed, transport bed, fluidized bed, moving bed, shell and tube, or trickle bed reactors. Preferred reactor types are continuously stirred tank reactors, bubble columns or loop reactors. More preferably, the process of this invention is conducted in a cascade of 2 to 10, more preferably 2 to 7, most preferably 3 to 5 reactors, and oxygen or an oxygen-containing gas and/or olefin is added in several portions to several reactors. The feed points for the addition of oxygen or an oxygen-containing gas and/or olefin are preferably located between the reactors.

Alternatively, the process of this invention can be conducted in a baffled tank reactor or in a plug flow reactor and oxygen or an oxygen-containing gas and/or olefin is added in several portions at several feed points to the reactor, that is, at several reactor stages.

Preferably, an additional amount of i) oxygen or an oxygen-containing gas or ii) olefin and oxygen or an oxygen-containing gas is added in step b) of the present invention. This embodiment of the present invention is more preferred than the addition of an olefin alone in step b) of the present invention.

It is understood that the embodiments of the invention can be combined. For example, the process of this invention can be carried out in a cascade of two or more baffled tank reactors and/or plug flow reactors or in a cascade of a baffled tank reactor and/or plug flow reactor in combination with another reactor.

Most preferably, the process of the present invention is conducted in a baffled tank reactor or in a plug flow reactor or in a cascade of 2 to 10, more preferably 2 to 7, most preferably 3 to 5 reactors, and oxygen or an oxygen-containing gas and optionally olefin is added to each of the reactors or reactor stages. In this preferred embodiment of the present invention, step a) is conducted in a first reactor or reactor stage, the mixture obtained in step a) is transferred in batches or, more preferably, continuously, to a second reactor or reactor stage to which an additional amount of oxygen or an oxygen-containing gas and optionally olefin is added and the reaction is continued. Optionally the mixture obtained in the second reactor (stage) is transferred in batches or, more preferably, continuously, to a third reactor or reactor stage to which an additional amount of i) oxygen or an oxygen-containing gas and/or ii) olefin is added. The reaction obtained in the third reactor (stage) can be transferred to a forth reactor or reactor stage and reacted with an additional amount of oxygen and so on. The residence time of the mixture in each reactor (stage) generally is from 0.5 to 45 minutes, preferably from 1 to 30 minutes, most preferably from 1 to 20 minutes, depending on the applied pressure and temperature.

Before an additional amount of i) oxygen or an oxygen-containing gas and/or ii) olefin is added to the mixture produced in step a), a portion of the produced olefin oxide, non-reacted olefin and/or by-product may be removed from the produced mixture.

The amount of oxygen or an oxygen-containing gas added in step a) generally is from 1 to 99 percent, preferably from 2 to 98 percent, more preferably from 6 to 94 percent, most preferably from 20 to 80 percent, based on the total amount of oxygen or oxygen-containing gas added during the liquid phase process.

Preferably, the total amount of oxygen or oxygen-containing gas to be added during the liquid phase process is divided into 2 to 100, more preferably 3 to 15, most preferably 3 to 8 portions which may be equal, about equal or unequal, whereby the first portion is added in step a) and the remaining portion(s) is/are added in step b).

The amount of olefin added in step a) generally is from 1 to 100 percent, preferably from 2 to 98 percent, more preferably from 6 to 94 percent, most preferably from 20 to 80 percent, based on the total amount of olefin added during the liquid phase process.

The product mixture obtained in the present invention generally contains from 30 to 90 percent, typically from 40 to 70 percent of solvent, generally from 0.2 to 6.0 percent, typically from 0.5 to 5 percent of olefin oxide, generally from 9.8 to 60 percent, typically from 20 to 40 percent of non-converted olefin, based on the total weight of the liquid product mixture, the remaining amount being by-products, such as carbon dioxide, or oxygenated by-products, like water, aldehydes, such as acetaldehyde; ketones, such as acetone or 1-hydroxy-2-propanone; alcohols, such as 2-propanol or allyl alcohol; glycols, such as 1,2-propane diol; esters, such as methyl formate, methyl acetate or 1,2-propane glycol diacetate; acids, such as formic acid, acetic acid or propionic acid; acetals such as 2-ethyl-4-methyl-1,3-dioxolane, 2,4-dimethyl-1,3-dioxolane or 2,2,4-trimethyl-1,3-dioxolane; or ethers such as 1-methoxy-2-propanone.

The produced mixture can be separated into the individual components by known means, such as distillation.

Surprisingly, it has been found that in the process of the present invention the required amount of solvent per unit of produced olefin oxide can generally be reduced by 40 percent or more, in many cases even by 50 percent or more, under optimised conditions even by 70 percent or more, as compared to a process wherein the oxygen is added in one portion to the reaction mixture. At the same time it has been found that in the process of the present invention the amount of propene, that has to be recycled per unit of produced olefin oxide, can generally be reduced by 40 percent or more, in many cases even by 60 percent or more, under optimised conditions even by 75 percent or more.

The invention is illustrated by the following examples which should not be construed to limit the scope of the present invention. Unless stated otherwise all parts and percentages are given by weight.

EXAMPLE 1

1A. (Comparative Example)

6.3 Mol/hour of o-dichlorobenzene, 11.2 mol/hour of propene, 5.0 mol/hour of nitrogen and 1.5 mol/hour of oxygen (resulting in an oxygen concentration of 22.9 volume percent) were fed into a continuously stirred tank reactor. The reaction temperature was 165° C., the reaction pressure was 54 bar (5.4 MPa) and the average residence time was 13 minutes.

The mixture obtained in 1.A. was cooled down to ambient temperature and after depressurizing it was divided in a gaseous and a liquid product stream. Samples of both streams were collected in a vent and a liquid sampling drum respectively and analyzed.

The propene conversion was 11.4 mol percent and the selectivity to propylene oxide was 42.9 mol percent. The overall selectivity to propylene oxide, propylene glycol and their consecutive products as 57.7 mol percent. The selectivity to carbon dioxide was 9.2 mol percent, to formic acid 5.7 mol percent, to acetic acid 4.0 mol percent and to propylene glycol 3.1 mol percent. 15.9 mol percent of the reacted propene can be detected as oxygenates. Residual products were organic by-products.

The process according to 1.A. required 29.6 weight parts of solvent per weight part of produced propylene oxide and lead to a propene recycle stream of 14.8 weight parts per weight part of produced propylene oxide.

1B. Staged Addition Process

The mixture obtained in step 1.A. (containing 8.6 mol/hour of o-dichlorobenzene, 0.8 mol/hour of propylene oxide, 0.2 mol/hour of formic acid and 13.9 mol/hour of propene), 1.7 mol/hour of fresh propene, 6.9 mol/hour of nitrogen and 2.0 mol/hour of oxygen (resulting in an oxygen concentration of 22.9 volume percent) were fed into a second continuously stirred tank reactor. The reaction temperature was 165° C., the reaction pressure was 54 bar (5.4 MPa) and the average residence time was 9 minutes.

The obtained mixture was cooled down to ambient temperature and after depressurizing it was divided in a gaseous and a liquid product stream. Samples of both streams were collected in a vent and a liquid sampling drum respectively and analyzed. For the individual reaction step described in example 1B the propene conversion was 11.8 percent, the selectivity to propylene oxide was 41.4 mol percent, the overall selectivity to propylene oxide, propylene glycol and their consecutive products was 60.0 mol percent, the selectivity to carbon dioxide was 8.2 mol percent, to formic acid 6.0 mol percent, to acetic acid 3.5 mol percent and to propylene glycol 2.4 mol percent. 14.5 mol percent of the reacted propene can be detected as oxygenates. Residual products were organic by-products.

For the entire two-step process according to Example 1 the propene conversion was 20.8 mol percent and the selectivity to propylene oxide was 42.1 percent. The entire two-step process according to Example 1 required 14.8 weight parts of solvent per weight part of produced propylene oxide and lead to a propene recycle stream of 6.5 weight parts per weight part of produced propylene oxide. This means that the entire two-step process of Example 1 required only 50 percent solvent, compared to the amount used in Comparative Example 1.A., and that the amount of the propene recycle stream in the entire two-step process according to Example 1 was only 44 percent of the amount of the propene recycle stream in Comparative Example 1.A. (per unit of produced propylene oxide).

EXAMPLE 2

2A. (Comparative Example)

8.7 Mol/hour of o-dichlorobenzene, 15.4 mol/hour of propene, 6.9 mol/hour of nitrogen and 2.0 mol/hour of oxygen (resulting in an oxygen concentration of 22.8 volume percent) were fed into a continuously stirred tank reactor. The reaction temperature was 165° C., the reaction pressure was 54 bar (5.4 MPa) and the average residence time was 9 minutes The mixture obtained in 2A. was cooled down to ambient temperature and after depressurizing it was divided in a gaseous and a liquid product stream. Samples of both streams were collected in a vent and a liquid sampling drum respectively and analyzed. The propene conversion was 5.7 percent and the selectivity to propylene oxide was 49.4 mol percent. The overall selectivity to propylene oxide, propylene glycol and their consecutive products was 61.2 mol percent. The selectivity to carbon dioxide was 6.9 mol percent, to formic acid 6.3 mol percent, to acetic acid 2.9 mol percent and to propylene glycol 2.1 mol percent. 17.9 mol percent of the reacted propene can be detected as oxygenates. Residual products were organic by-products.

The process according to 2A. required 51.4 weight parts of solvent per weight part of produced propylene oxide and lead to a propene recycle stream of 25.7 weight parts per weight part of produced propylene oxide.

2B. Staged addition process

The mixture obtained in step 2A. (containing 6.2 mol/hour of o-dichlorobenzene, 0.3 mol/hour of propylene oxide, 0.1 mol/hour of formic acid and 10.5 mol/hour of propene), 0.7 mol/hour of fresh propene, 5.0 mol/hour of nitrogen and 1.5 mol/hour of oxygen (resulting in an oxygen concentration of 22.8 volume percent) were fed into the second continuously stirred tank reactor. The reaction temperature was 165° C., the reaction pressure was 54 bar (5.4 MPa) and the average residence time was 13 minutes.

The obtained mixture was cooled down to ambient temperature and after depressurizing it was divided in a gaseous and a liquid product stream. Samples of both streams were collected in a vent and a liquid sampling drum respectively and analyzed. For the individual reaction step described in Example 2B the propene conversion was 10.5 percent, the selectivity to propylene oxide is 37.8 mol percent, the overall selectivity to propylene oxide, propylene glycol and their consecutive products is 57.8 mol percent, the selectivity to carbon dioxide was 10.0 mol percent, to formic acid 3.2 mol percent, to acetic acid 4.2 mol percent and to propylene glycol 3.1 mol percent. 15.9 mol. percent of the reacted propene can be detected as oxygenates. Residual products were organic by products.

For the entire two-step process according to Example 2 the propene conversion is 15,3 mol percent and the selectivity to propylene oxide is 41,9 mol percent. The entire two-step process according to Example 2 requires 21.3 weight parts of solvent per weight part of produced propylene oxide and leads to a propene recycle stream of 9.6 weight parts per weight part of produced propylene oxide. This means that the entire twostep process of Example 2 requires only 42 percent solvent, compared to the amount used in comparative Example 2A., and that the amount of the propene recycle stream in the entire two-step process according to Example 2 is only 38 percent of the amount of the propene recycle stream in Comparative Example 2A. (per unit of produced propylene oxide).

EXAMPLE 3

3A. (Comparative Example)

Comparative Example 2A. is repeated.

3B. Staged Addition Process

Like in Example 28, the mixture obtained in step 2A. was used as a starting material, except that a higher volume/hour was fed into the reactor to achieve a lower residence time. The mixture obtained in step 2A. (containing 8.7 mol/hour of o-dichlorobenzene, 0.5 mol/hour of propylene oxide, 0.1 mol/hour of formic acid and 14.8 mol/hour of propene), 0.9 mol/hour of fresh propene, 6.9 mol/hour of nitrogen and 2.0 mol/hour of oxygen (resulting in an oxygen concentration of 22.9 volume percent) were fed into a second continuously stirred tank reactor. The reaction temperature was 165° C., the reaction pressure was 54 bar (5.4 MPa) and the average residence time was 9 minutes.

The obtained mixture was cooled down to ambient temperature and after depressurizing it was divided in a gaseous and a liquid product stream. Samples of both streams are collected in a vent and a liquid sampling drum respectively and analyzed. For the individual reaction step described in example 3B the propene conversion was 10.2 percent, the selectivity to propylene oxide was 40.5 mol percent, the overall selectivity to propylene oxide, propylene glycol and their consecutive products was 55.7 mol percent, the selectivity to carbon dioxide was 9.6 mol percent, to formic acid 6.3 mol percent, to acetic acid 3.8 mol percent and to propylene glycol 2.3 mol percent. 24.3 mol percent of the reacted propene can be detected as oxygenates. Residual products were organic by-products.

For the entire two-step process according to Example 3 the propene conversion was 15.0 mol percent and the selectivity to propylene oxide was 43.7 mol percent. The entire two-step process according to Example 3 required 20.8 weight parts of solvent per weight part of produced propylene oxide and leads to a propene recycle stream of 9.4 weight parts per weight part of produced propylene oxide. This means that the entire two-step process of Example 3 requires only 41 percent solvent, compared to the amount used in comparative Example 2A. and that the amount of the propene recycle stream in the entire two-step process according to Example 3 was only 37 percent of the amount of the propene recycle stream in Comparative Example 2A. (per unit of produced propylene oxide).

3C. Staged Addition Process

The mixture obtained in step 3B. (containing 8.7 mol/hour of o-dichlorobenzene, 1.2 mol/hour of propylene oxide, 0.2 mol/hour of formic acid and 14.1 mol/hour of propene), 1.6 mol/hour of fresh propene, 6.9 mol/hour of nitrogen and 2.0 mol/hour of oxygen (resulting in an oxygen concentration of 22.5 volume percent) were fed into the third continuously stirred tank reactor. The reaction temperature was 165° C., the reaction pressure was 54 bar (5.4 MPa) and the average residence time was 9 minutes.

The obtained mixture was cooled down to ambient temperature and after depressurizing it was divided in a gaseous and a liquid product stream. Samples of both streams were collected in a vent and a liquid sampling drum respectively and analyzed. For the individual reaction step described in Example 3C. the propene conversion was 10.3 percent, the selectivity to propylene oxide was 32.6 mol percent, the overall selectivity to propylene oxide, propylene glycol and their consecutive products was 54.6 mol percent, the selectivity to carbon dioxide was 9.0 mol percent, to formic acid 6.2 mol percent, to acetic acid 4.6 mol percent and to propylene glycol 4.1 mol percent. 16.2 mol percent of the reacted propene can be detected as oxygenates. Residual products are organic by-products.

For the entire three-step process according to Example 3 the propene conversion was 22.6 mol and the selectivity to propylene oxide was 39.3 mol. The entire three-step process according to Example 3 required 14.1 weight parts of solvent per weight part of produced propylene oxide and lead to a propene recycle stream of 6.3 weight parts per weight part of produced propylene oxide. This means that the entire three-step process of Example 3 required only 28 solvent, compared to the amount used in comparative Example 2.A. and that the amount of the propene recycled stream in the entire three-step process of Example 3 was only 25 percent of the amount of the propene recycled stream in Comparative Example 2A. (per unit of produced propylene oxide).

What is claimed is:

1. A liquid phase process for preparing an olefin oxide from an olefin in a cascade of two or more reactors, in a baffled tank reactor or in a plug flow reactor comprising the steps of
    a) contacting the olefin in a solvent with oxygen or an oxygen-containing gas in a first reactor of the reactor cascade or in a first stage of the baffled tank reactor or of the plug flow reactor, thereby producing a mixture comprising olefin oxide, non-converted olefin, solvent and by-products and
    b) transferring at least a portion of the mixture obtained in step a) to a second reactor of the reactor cascade or to a second stage of the baffled tank reactor or plug flow reactor, adding an additional amount of i) oxygen or an oxygen-containing gas and/or ii) olefin to the mixture and continuing the reaction.

2. The process of claim 1 wherein the reaction is conducted at a temperature of from 100° C. to 210° C. and a pressure of from 20 to 100 bar (2 to 10 MPa).

3. The process of claim 1 wherein an additional amount of i) oxygen or an oxygen-containing gas or ii) olefin and oxygen or an oxygen-containing gas is added in one or more stages or continuously.

4. The process of claim 1 wherein the amount of oxygen or an oxygen-containing gas added in step a) is from 6 to 94 percent, based on the total amount of oxygen or oxygen-containing gas added during the liquid phase process.

5. The process of claim 1 wherein the reaction is conducted in a plug flow reactor or baffled tank reactor and oxygen or an oxygen-containing gas and/or olefin is added in several portions at several feed points to the reactor.

6. The process of claim 1 wherein the reaction is conducted in a cascade of from 2 to 10 reactors and oxygen or an oxygen-containing gas and/or olefin is added to each of these reactors.

7. The process of claim 1 wherein the olefin is propylene.

8. The process of claim 1 wherein the solvent has a boiling point above 130° C.

9. The process of claim 8 wherein the solvent is a halogenated benzene.

10. The process of claim 9 wherein the solvent is o-dichlorobenzene or m-dichlorobenzene.

11. The process of claim 2 wherein an additional amount of i) oxygen or an oxygen-containing gas or ii) olefin and oxygen or an oxygen-containing gas is added in one or more stages or continuously.

12. The process of claim 2 wherein the amount of oxygen or an oxygen-containing gas added in step a) is from 6 to 94 percent, based on the total amount of oxygen or oxygen-containing gas added during the liquid phase process.

13. The process of claim 2 wherein the reaction is conducted in a plug flow reactor or baffled tank reactor and oxygen or an oxygen-containing gas and/or olefin is added in several portions at several feed points to the reactor.

14. The process of claim 12 wherein the reaction is conducted in a plug flow reactor or baffled tank reactor and oxygen or an oxygen-containing gas and/or olefin is added in several portions at several feed points to the reactor.

15. The process of claim 2 wherein the reaction is conducted in a cascade of from 2 to 10 reactors and oxygen or an oxygen-containing gas and/or olefin is added to each of these reactors.

16. The process of claim 12 wherein the reaction is conducted in a cascade of from 2 to 10 reactors and oxygen or an oxygen-containing gas and/or olefin is added to each of these reactors.

17. The process of claim 2 wherein the olefin is propylene.

18. The process of claim 12 wherein the olefin is propylene.

19. The process of claim 18 wherein the solvent is a halogenated benzene.

20. The process of claim 19 wherein the solvent is o-dichlorobenzene or m-dichlorobenzene.

* * * * *